(12) United States Patent
Bermudes

(10) Patent No.: US 9,200,251 B1
(45) Date of Patent: Dec. 1, 2015

(54) BACTERIAL METHIONINE ANALOGUE AND METHIONINE SYNTHESIS INHIBITOR ANTICANCER, ANTIINFECTIVE AND CORONARY HEART DISEASE PROTECTIVE MICROCINS AND METHODS OF TREATMENT THEREWITH

(76) Inventor: David Gordon Bermudes, Woodland Hills, CA (US)

( * ) Notice: Subject to any disclaimer, the term of this patent is extended or adjusted under 35 U.S.C. 154(b) by 259 days.

(21) Appl. No.: 13/433,589

(22) Filed: Mar. 29, 2012

Related U.S. Application Data

(60) Provisional application No. 61/470,446, filed on Mar. 31, 2011.

(51) Int. Cl.
*A01N 63/00* (2006.01)
*C12N 1/20* (2006.01)
*C12N 15/63* (2006.01)
*G01N 33/569* (2006.01)

(52) U.S. Cl.
CPC ............... *C12N 1/20* (2013.01); *G01N 33/569* (2013.01)

(58) Field of Classification Search
None
See application file for complete search history.

(56) References Cited

U.S. PATENT DOCUMENTS

2004/0229338 A1* 11/2004 King ........................ 435/252.3
2005/0159349 A1* 7/2005 Soto et al. ..................... 514/12

OTHER PUBLICATIONS

Aguilar et al. Antimicrobial Agents and Chemotherapy. 21(3);381-386:1982.*
J C Perez-Diaz and R C Clowes, "Physical characterization of plasmids determining synthesis of a microcin which inhibits methionine synthesis in Escherichia coli.", J. Bacteriol. 1980, 141(3):1015.
Baquero, F., D. Bouanchand, MA C. Martinez-Perez, and C. Fernandez. 1978. 12 14 16 Microcin plasmids: a group of extrachromosomal elements coding for low-molecular-weight antibiotics in Escherichia coli. J. Bacteriol. 135:342-347.
Graham James O'brien, Molecular Analysis of Microcin 24: Genetics, Secretion and Mode of Action of a Novel Microcin. Ph.D. thesis, the University of Canterbury (1996).
Jose L. Martinez and Jose C. Perez-Diaz, "Isolation, Characterization, and Mode of Action on Escherichia coli Strains of Microcin D93", Antimicrobial Agents and Chemotherapy, Mar. 1986, p. 456-460 vol. 29, No. 3 (1986).

* cited by examiner

*Primary Examiner* — Amber D Steele
*Assistant Examiner* — Schuyler Milton
(74) *Attorney, Agent, or Firm* — Steven M. Hoffberg, Esq.; Ostrolenk Faber LLP

(57) ABSTRACT

A substantially purified substance having the properties of a bacterial microcin methionine analog, methionine synthesis inhibitor, tRNA-methionine synthase inhibitors or methionine competitive inhibitor capable of inhibiting tumor cell growth without inhibiting the growth of normal cells or treating neoplastic diseases, and may be used alone or in combination with other anti-cancer agents. The purified substance may also have anti-hyperhomocysteineuria and/or anti-infective properties, such as antifungal activity. The purified substance can be safely administered to animals including humans for the treatment of neoplastic, hyperhomocysteinemia and/or infectious diseases for the treatment of those diseases.

20 Claims, No Drawings

BACTERIAL METHIONINE ANALOGUE AND METHIONINE SYNTHESIS INHIBITOR ANTICANCER, ANTIINFECTIVE AND CORONARY HEART DISEASE PROTECTIVE MICROCINS AND METHODS OF TREATMENT THEREWITH

1. FIELD OF THE INVENTION

The present invention relates to bacterial microcins, methionine analogues, tRNA-methionine synthase inhibitors, and methionine synthesis inhibitors and their pharmaceutical use.

2. BACKGROUND OF THE INVENTION

Citation or identification of any reference herein, or any section of this application shall not be construed as an admission that such reference is available as prior art to the present application. The disclosures of each of these publications and patents are hereby incorporated by reference in their entirety in this application, and shall be treated as if the entirety thereof forms a part of this application.

Microcins are a class of bacteriocin antibacterial products produced by bacteria with the ability to directly or indirectly kill or inhibit other bacterial species (Duquesne et al., 2007, Microcins, gene-encoded antibacterial peptides from enterobacteria, Natural Product Reports, 24: 708-734, Hen and Jack, Chapter 13 Microcins, in Kastin (ed.), 2006, Handbook of Biologically Active Peptides, Academic Press; Alouf and Popoff (eds.), 2006, Comprehensive Sourcebook of Bacterial Protein Toxins, Third Edition, Academic Press). Use of bacteriocins, including colicins and microcins, for the treatment of cancer has previously been suggested (WO 2001/014579; WO 2003/074554). However, the use of methionine analogue or microcin methionine synthesis inhibitors, methionine analogues, derivatives or isomers, or tRNA-methionine synthase inhibitors has not previously been suggested for the treatment of cancer.

Coronary heart disease is associated with elevated levels of homocysteine (hyperhomocysteinemia; Eikelboom et al., 1999, Homocysteine and cardiovascular disease: a critical review of the epidemiologic evidence. Ann Intern Med. 131: 363-375). Homocysteine is a homologue of the amino acid cysteine containing an additional methylene ($—CH_2$) group. It is synthesized from methionine by the removal of the methyl group, and can be reconverted to methionine by re-addition of the methyl group. Treatments for hyperhomocysteinemia include betaine, which enhances the reconversion of homocysteine to methionine. Suggested treatments have also included thetin for enhancing the conversion of homocysteine to methionine (U.S. Pat. No. 5,668,173). Methods for measuring methionine (WO 2005/070014), S-adenosyl-methionine (SAM; WO 2001/051651) cysteine (WO 2003/044220) and homocysteine levels have been described (U.S. Pat. No. 6,020,206; WO 2001/000853; WO 2004/023097) and are known to those skilled in the art. Treatments blocking conversion of methionine to homocysteine using bacterial microcins, methionine analogues, tRNA-methionine synthase inhibitors or methionine synthesis inhibitors have not been previously suggested.

Methionine analogues described by Bassiri and Rahimi-Larijani (WO/201001493) did not include microcins as methionine analogues or inhibitors of methionine metabolism. Bacterial species are known to be susceptible to agents such as bacteriocins including microcins. However, methionine analogue microcins have not been suggested to have broad antiinfective activity. The types of infectious diseases for which methionine analogue microcins are effective may generally include prions, viruses (e.g., hepatitis C), bacteria (e.g., *Staphylococcus aureus, Pseudomonas aeruginosa*), protozoans (e.g., *Entamoeba histolytica, plasmodium falciparum*), fungi (e.g., *Candida albicans, Pneumocystis carnii*) and helminthes (e.g., *Ancylostoma duodenale, Schistosoma mansoni*), (Mandell, Bennett and Dolin 2010, Principles and Practices of Infectious Diseases, $7^{th}$ Edition, Elsevier Publishers, 4320 pages).

3. SUMMARY OF THE INVENTION

3.1 Therapeutic Molecules

The present invention provides pharmaceutical agents for use in treating animals which are, or are derived from, bacterial microcins.

These compositions, for example in pharmaceutical formulations, may be used to treat neoplastic diseases, and coronary heart diseases (CHD). The agents are well tolerated, suppress methionine intolerance in CHD and exhibit toxicity to tumor cells with reduced toxicity to normal cells. The agents may also be used to treat infectious diseases.

These microcins (or related compositions) can be formed synthetically, semi-synthetically, or purified from culture media.

In another embodiment, a microcin, methionine analogue, tRNA-methionine synthase inhibitors or methionine synthesis inhibitor-producing organism, e.g., a genetically engineered organism or a wild type probiotic organism, may itself form part of a therapy (e.g., WO/2008/155120 Methods And Compositions For Treating Mucositis; WO/2008/090223 Treatment Of Immune Disease By Mucosal Delivery Of Antigens Using Genetically Modified *Lactobacillus*; WO/2001/025397 Compositions And Methods For Tumor-Targeted Delivery Of Effector Molecules). Typically, a genetically engineered organism with defined and desirable traits is employed, such as attenuation to avoid unintended pathology, and susceptibility to antibiotics in case eradication is required. A live bacteria may be administered, for example, either systemically (e.g., parenteral, intravenous, intramuscular, intralymphatic, intradermal, subcutaneous) or to the mucosal system through oral, nasal, intravessically or suppository administration. Probiotic bacteria include *Lactobacillus* sp., *Lactococcus* sp., *Leuconostoc* sp., *Pediococcus* sp., *Streptococcus* sp., *Lactococcus* sp., *Bacillus* sp., *Bifidobacterium* sp., *Bacteroides* sp., and *Escherichia coli* such as the 1917 Nissel strain. The probiotic bacteria may also include attenuated pathogenic bacteria such as attenuated *Salmonella typhimurium* (e.g., VNP20009) or other *Salmonella* serotypes, or attenuated *Streptococcus*, such as *S. agalactiae*. Other bacterial strains are also encompassed, including non-pathogenic bacteria of the gut such as *E. coli* strains, *Bacteriodies*, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphalococcus* sp., *Yersinia* sp., *Streptococcus* sp., and *Listeria* sp. Bacteria of low pathogenic potential to humans such as insect pathogenic *Xenorhabdus* sp., *Photorhabdus* sp. and human wound *Photorhabdus* (*Xenorhabdus*) are also encompassed. It is known to those skilled in the art that minor variations in molecular biology techniques between gram-negative and gram-positive organisms, such as use of gram-positive origins of replication, gram-positive signal sequences gram-positive promoters (e.g., *Lactococcus* expression, Mohamadzadeh et al., PNAS Mar. 17, 2009 vol. 106 no. 11 4331-4336) are required and substituted as needed.

The present invention also employs, for example, isolated or substantially purified bacterial microcin methionine analogues or methionine synthesis inhibitor introduced either systemically (e.g., parenteral, intravenous (IV), intramuscular (IM), intralymphatic (IL), intradermal (ID), subcutaneously (sub-q), local-regionally (e.g., intralesionally, intratumorally (IT), intraperitoneally (IP), topically, intrathecally, by inhaler or nasal spray) or to the mucosal system through oral, nasal, pulmonary intravesically, enema or suppository administration where they become biologically available and thereby provide a therapeutic benefit by reducing or eliminating the disease, malignancy and/or neoplasia. The level or isolation or purification is dependent on pharmacological acceptability of the respective formulation, and absence of interfering or toxic substances.

The microcins are produced and purified from bacterial cultures by methods known to those skilled in the art for the purification of amino acids, including all forms of chromatography, ion exchange, electrophoresis, differential extractions, precipitations (e.g., Faurie and Thommel (eds) 2003, Microbial production of L-amino acids. Springer; Kumar and Gomes, 2005, Methionine production by fermentation, Biotechnology Advances 23: 41-61). Endotoxin (bacterial lipopolysaccharides; LPS) are removed using methods known to those skilled in the art (US20030036175, U.S. Pat. No. 7,109,322, U.S. Pat. No. 7,510,826, Colpan et al., Process for the depletion or removal of endotoxins; U.S. Pat. No. 6,297,371 Colpan et al., Process for the preparation of endotoxin-free or endotoxin-depleted nucleic acids and/or oligonucleotides for gene therapy, each of which is expressly incorporated herein by reference).

The types of cancers or neoplasias to which the present invention is or may be directed include all neoplastic malignancies, including solid tumors such as those of colon, lung, breast, prostate, sarcomas, carcinomas, head and neck tumors, melanoma, as well as hematological, non-solid or diffuse cancers such as leukemia and lymphomas, myelodysplastic cells, plasma cell myeloma, plasmacytomas, and multiple myelomas.

The types of metabolic disorders include those for which methionine plays a central role, including but not limited to hypercysteinemia.

The types of infectious diseases for which methionine analogue or methionine synthesis inhibitor microcins are effective may generally include prions, viruses (e.g., hepatitis C), bacteria (e.g., *Staphylococcus aureus*, *Pseudomonas aeruginosa*), protozoans (e.g., *Entamoeba histolytica*, *plasmodium falciparum*), fungi (e.g., *Candida albicans*, *Pneumocystis carnii*) and helminthes (e.g., *Ancylostoma duodenale*, *Schistosoma mansoni*), (Mandell, Bennett and Dolin 2010, Principles and Practices of Infectious Diseases, 7th Edition, Elsevier Publishers, 4320 pages).

4. OBJECTS OF THE INVENTION

The present invention provides, according to one embodiment, substantially purified microcins, methionine analogues or methionine synthesis inhibitors that have antineoplastic activity and provide a benefit to a patient with cancer or other forms of neoplastic disease. In a preferred embodiment, the tumor types treated by the microcins, methionine analogues, tRNA-methionine synthase inhibitors or methionine synthesis inhibitors are generally deficient in methylthioadenosine phosphorylase (MTAP). In another embodiment, the microcins, methionine analogues, tRNA-methionine synthase inhibitors or methionine synthesis inhibitors are used as part of a combination chemotherapy. In a preferred embodiment, the methionine analogues or methionine synthesis inhibitor are used in combination with a chemotherapeutic agent. In another preferred embodiment, the microcins, methionine analogues, tRNA-methionine synthase inhibitors or methionine synthesis inhibitors are used in combination with methioninase. In another embodiment, the substantially purified microcins, methionine analogues, tRNA-methionine synthase inhibitors or methionine synthesis inhibitors provide a benefit to a patient with hyperhomocysteinemia by reducing or inhibiting the conversion of homocysteine from methionine. In another embodiment, the microcins, methionine analogues, tRNA-methionine synthase inhibitors or methionine synthesis inhibitors are used for the treatment of infectious diseases. In another embodiment, a pharmaceutical composition comprises a pharmaceutically acceptable carrier and one or more microcin methionine analogs or methionine synthesis inhibitors.

The present invention encompasses, for example, treatment protocols that provide a better therapeutic effect than current existing anticancer therapies. In particular, the present invention provides methods for prophylaxis or treatment of neoplastic diseases in a subject comprising administering to said subject and one or more methionine analogue microcins or methionine synthesis inhibitors. Accordingly, when administered to an individual, a microcins, methionine analogues, tRNA-methionine synthase inhibitors or methionine synthesis inhibitors, in accordance with the present invention, results in anti-neoplastic activity.

The present invention encompasses treatment protocols that provide a better therapeutic effect than current existing anti-hyperhomocysteinemia therapies. In particular, the present invention provides methods for prophylaxis or treatment of hyperhomocysteinemia in a subject comprising administering to said subject and one or more microcins, methionine analogues, tRNA-methionine synthase inhibitors or methionine synthesis inhibitors. Accordingly, when administered to an individual, a microcins, methionine analogues, tRNA-methionine synthase inhibitors or methionine synthesis inhibitors, in accordance with the present invention, results in anti-hyperhomocysteinemia.

It is therefore an object to provide a method of treating an animal, comprising administering an effective dose of at least one pharmaceutically acceptable microcin, methionine analogue or methionine synthesis inhibitor, to an animal having at least one of a tumor, hyperhomocysteinemia, and an infectious disease, to thereby respectively inhibit tumor growth, treat hyperhomocysteinemia, or treat the infectious disease.

It is a further object to provide a method of treating an animal, comprising: determining a presence of a disease selected from the group consisting of a neoplasia, hyperhomocysteinemia, and an infectious disease; administering a regimen of effective doses of a pharmaceutically acceptable composition comprising at least one of isolated microcins, methionine analogues, and or methionine synthesis inhibitors, to an animal having the disease, over a sufficient time to achieve an effective treatment of the disease; and monitoring the treatment by performing at least one laboratory test to determine at least one of a neoplasm size, a homocystiene level, and a presence of an infectious organism.

It is also an object to provide a pharmaceutical composition for administration to a human, comprising at least one pharmaceutically acceptable agent selected from the group consisting of microcins, methionine analogues and methionine synthesis inhibitors, which has been substantially purified, in unit dose form.

The pharmaceutically acceptable microcin, methionine analogue or methionine synthesis inhibitor with tumor growth inhibitory ability may be administered in combination with a microtubule depolymerizing agent. The microtubule inhibitory agent may comprise at least one of vincristine, vinorelbine, vinblatine and mebendazol.

The at least one pharmaceutically acceptable microcin, methionine analogue, or methionine synthesis inhibitor may be administered in combination with methioninase. Methioninase may be concurrently administered during the regimen.

The pharmaceutically acceptable composition may comprise a purified methionine analog microcin, or a purified methionine synthesis inhibitor microcin. The pharmaceutically acceptable microcin, methionine analogue or methionine synthesis inhibitor comprises a microcin which is at least one of (a) derived from *E. coli* LP 136, *E. coli* LP-93 and *E. coli* LP15, D93, N-15, V517; (b) encoded by at least one plasmid selected from the group consisting of plasmid pCP101, pCP102, pCP103, pCP104, pCP105, pCP106, and pVA517C; and (c) microcin 15m.

The animal may have an infectious disease caused by a fungus. The fungus may comprise at least one of *Pneumocystis carnii* and *Candida albicans*.

The animal may have a tumor comprising a neoplasia originating in a tissue selected from the group consisting of stomach, colon, rectum, liver, pancreas, lung, breast, cervix uteri, corpus uteri, ovary, prostate, testis, bladder, kidney, brain, central nervous system, head, neck, throat, or selected from the group consisting of Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney and lymphoma cancer.

The pharmaceutical composition may further comprise a pharmaceutically acceptable excipient, additive or carrier. The unit dose form may comprise an intravenous dosage vial, or an oral unit dosage form, or a parenteral dosage form.

5. DEFINITIONS

In order that the invention may be more fully understood, the following terms are defined.

The phrase "effective amount" is used throughout the specification to describe an amount of the present compound or composition which is used to effect an intended result. In most aspects of the present invention the term effective amount is used in conjunction with the treatment of a patient suffering from neoplasia to prevent the further growth of the neoplasms, to bring that growth under control or even kill cancerous cells and preferably, produce a remission of the tumor. In other aspects of the present invention the term effective amount is used in conjunction with the treatment of a patient suffering from hyperhomocysteinuria to prevent the further conversion of methionine to homocysteine.

The phrase "substantially purified" means a preparation having better than 80% purity, preferably more than 90% pure and more preferably greater than 95% pure, more preferably greater than 97% pure, more preferably greater than 99% pure. Purity in this case refers to compounds having specific biological activity of the desired composition(s), and may comprise a plurality of compositions which together have the desired specific biological activity. The purification is intended to remove contaminants derived from the production process or source, and is not intended to exclude intentionally added or retained components. After purification, the composition may be diluted or otherwise compounded with other active or inactive ingredients.

The term "coadministered" is used to describe the administration of a compound according to the present invention in combination with another drug, to a patient, regardless of the time of administration, such that effective amounts of the present compounds and the coadministered drugs are present in the patient at the same time during therapeutic treatment.

As used herein, the term "analog" or "analogue" refers to a compound that possesses a similar or identical sub-structure as another molecule, such as an amino acid molecule, or to be a competitive inhibitor thereof, but does not necessarily comprise a similar or identical function.

As used herein, the phrase "methionine synthesis inhibitor" refers to a component that may or may not possess similar or identical sub-structure as another molecule, such as an amino acid molecule, or amino acid analogue, but acts to inhibit the synthesis of the similar or identical sub-structure, such as the methionine amino acid.

As used herein, the phrase "unit dose form" refers to a pharmaceutically acceptable formulation packaged or otherwise provided in a form which is appropriate for administration in an integral multiple, or in some instances, a readily generated fraction, for a single patient at a single time. Thus, pills, capsules, single use ampoules, and the like are examples of unit dose forms.

6. DETAILED DESCRIPTION OF THE INVENTION

The present invention provides, according to various embodiments, substantially purified microcins, methionine analogues, tRNA-methionine synthase inhibitors or methionine synthesis inhibitors including homoserine O-succinyltransferase inhibitor therapeutic molecules. In particular, one aspect of the invention relates to treatment of cancer of an individual by eliciting a therapeutic response against cancer. The types of cancer may generally include solid tumors, carcinomas, leukemias, lymphomas and multiple myelomas. In addition, therapeutic microcins, methionine analogues, tRNA-methionine synthase inhibitors or methionine synthesis inhibitors including homoserine O-succinyltransferase inhibitors have enhanced activity when coadministered with methionine-depleting agents such as methioninase. Another aspect of the invention relates treatment of hyperhomocysteinemia by administering microcins, methionine analogues, tRNA-methionine synthase inhibitors or methionine synthesis inhibitors molecules to an individual to elicit a therapeutic response against excessive production of homcysteine from methionine. Another aspect of the invention relates to treatments of infectious diseases. The types of infectious diseases for which methionine analogue microcins are effective may generally include prions, viruses, bacteria, protozoans (protists), fungi (e.g., *Candida albicans, Pneumocystis carnii*) and helminthes (Mandell, Bennett and Dolin 2010, Principles and Practices of Infectious Diseases, 7th Edition, Elsiever Publishers, 4320 pages).

Microcin methionine analogues, methionine-competitive microcins, methionine synthesis inhibitors or isomers thereof including homoserine O-succinyltransferase inhibitors have been described directly or indirectly as antibacterial bacteriocin with antibacterial properties by several authors (Sanchez et al., 1986, Plasmid pVA517C from *Escherichia coli* V517 is required for the expression of an antibiotic microcin, J. Antbiotics (Tokyo) 39: 1028-1030; Martinez and Perez-Diaz 1990, Cloning the determinants for microcin D93 production and analysis of three different D-type microcin plasmids. Plasmid 23: 216-225; Aguilar et al., 1982, Microcin 15m from *Escherichia coli*: mechanism of antibiotic action, Antimicrobial Agents and Chemotherapy 21: 381-386, inhibits homoserine-O-transsuccinylase; Aguilar et al., 1983, Microcin 15n, a $2^{nd}$ antibiotic from *Escherichia coli* LP15, Journal of Antibiotics 36: 325-327; Aguilar et al., 1982, Mechanisms involved in the increased sensitivity of *Escherichia coli* to microcin 15M at 42 degrees C., Current Microbiol 7: 83-86; Blanco et al., 1986, Effect of growth rate and aeration on the production of microcin by *Escherichia coli* growing in continuous culture, Microbios 46: 59-64; Kurepina and Khmel 1986, Microcins: their nature and genetic determination, Mol. Gen. Mikrobiol Virusol 4: 3-9; Perez-Diaz and Clowes 1980, Physical characterization of plasmids determining synthesis of a microcin which inhibits methionine synthesis in *Escherichia coli*, J. Bacteriology 141: 1015-1023; Martinez and Perez-Diaz 1990, Cloning the determinants for microcin D93 production and analysis of three different D-type microcin plasmids, Plasmid 23: 216-225; Martinez and Perez-Diaz 1986, Isolation, characterization and mode of action on *Escherichia coli* strains of microcin D93, Antimicrobial Agents and Chemotherapy 29: 456-460; Sable et al., 2003, Wild-type *Escherichia coli* producing micrcins B17, D93, J25 and microcin L production and immunity, Can. J. Microbiology 49: 356-361). Methionine analogues, tRNA-methionine synthase inhibitors methionine isomers, methionine synthesis inhibitors including homoserine O-succinyltransferase inhibitors are produced by several bacterial strains containing microcin plasmids, including but not limited to *E. coli* LP 136, *E. coli* LP-93 and *E. coli* LP15, and are believed to be variously encoded by the plasmids pCP101, pCP102, pCP103, pCP104, pCP105, pCP106, and/or pVA517C. Isolation of new methionine analogue or methionine synthesis inhibitor microcins from animal, human, clinical, or environmental samples can be performed using standard techniques described by the authors above, including diffusion through a cellophane membrane and diminution of effect in the presence of excess methionine.

Methionine dependence is used as a guide for selection of cancerous, metabolic and infectious targets, such as solid tumors, hyperhomocysteinemia, or an infectious disease such as *Pneumocystis*. Methionine dependency has been described by Durando et al., 2008 (Methionine dependency of cancer cells; A new therapeutic approach? Bull Cancer 95: 69-76 and Mecham et al., 1983, The metabolic defect of methionine dependence occurs frequently in human tumor cell lines, Biochem. Biophys. Res. Comm. 117: 429-434) and treatments using methioninase have been described by Miki et al., 2000, Cancer Research 60: 2696-2702; Miki et al., 2000, Cancer Gene Therapy 7: 332-338; Tan et al., 1999 Clin Cancer Res 5: 2157-2163; Yoshido et al., 1998, Cancer research 58: 2583-2587).

For the treatment of cancer, therapeutic methionine microcin analogues are tested for cytotoxicity to cancer cells of different types (e.g., colon, lung, breast, prostate, stomach) and different genetic backgrounds (e.g., p53). The microcins, methionine analogues, tRNA-methionine synthase inhibitors or methionine synthesis inhibitors including homoserine O-succinyltransferase inhibitors may also be tested for effects on cancer cell signaling pathways (Adjei and Hidalgo 2005, Intracellular signal transduction pathway proteins as targets for cancer therapy, J. Clin Oncology 23: 5386-5403) and genotoxic stress pathways (Newton et al., 2004, The utility of DNA microarrays for characterizing genotoxicity, Environmental Health Perspectives 112: 420-422), and cross-referenced with the genetic background and tumor cell type. The effect of the microcins, methionine analogues, tRNA-methionine synthase inhibitors or methionine synthesis inhibitors on in vitro cytotoxicity is determined using standard cell culture techniques and cytotoxicity assays such as MTT (3-(4,5-Dimethylthiazol-2-yl)-2,5-diphenyltetrazolium bromide, a tetrazol; Mosmann 1983; J. Immunol Methods 65:55-63) known to those skilled in the art. The contribution of the microcins, methionine analogues, tRNA-methionine synthase inhibitors or methionine synthesis inhibitors and cytotoxic agents or methioninase are determined individually and in combination. Methioninase (methionine gamma-lyase) treatments have been previously described (WO 2000/029589; WO 1999/007858; WO 1996/040284; WO 1994/011535). Combination effects, including antagonism, additivity or synergy may determined using the median effect analysis (Chou and Talaly 1981 Eur. J. Biochem. 115: 207-216) or other standard methods (White et al., 1996, Antimicrobial Agents and Chemotherapy 40: 1914-1918; Brenner, 2002, Annals of Oncology 13: 1697-1698; Berenbaum M C. 1989. What is synergy? Pharmacol Rev. 41(2): 93-141; Greco W R, Bravo G, Parsons J C. 1995. The search for synergy: a critical review from a response surface perspective. Pharmacol Rev. 47(2): 331-85); Zhao et al., 2004, Evaluation of Combination Chemotherpy, Clin Cancer Res 10: 7994-8004; Loewe and Muischnek, 1926. Effect of combinations: mathematical basis of the problem, Arch. Exp. Pathol. Pharmakol. 114: 313-326). The assay may also be used to determine synergy, additivity or antagonism of two or more bacterial methionine analogue microcins. The assay may also be used to determine synergy, additivity or antagonism a bacterial methionine analogue microcins together with microtubule depolymerizing agents (vincristine, vinorelbine, vinblatine and mebendazole) conventional small molecule cytotoxin (e.g., cisplatin, doxorubicin, irinotecan, paclitaxel; Chu and DeVita, 2010, Physicians' Cancer Chemotherapy Handbook, Jones and Bartlett), targeted therapeutic (e.g., imatinib, irissa, cetuximab), proteosome inhibitors (e.g., bortezomib), mTOR inhibitors or PARP inhibitors. In vivo studies (G. K. Schwartz (ed) 2005, Combination cancer therapy: Modulators and potentiators, Human Press, Totowa, N.J., 284 pp.; B. A. Teicher and P. A. Andrews (eds.) 2004, Anticancer drug development guide, Preclinical screening, clinical trials and approval, Second Edition, Humana Press, Totowa, N.J., 450 p.; Teicher (ed.) 2002, Tumor models in cancer research, Human Press, Totowa, N.J., 690 p) may also be performed with antiangiogenic inhibitors such as Avastin, combrettastatin, thalidomide.

For the treatment of hyperhomocysteinemia, therapeutic microcins, methionine analogues, tRNA-methionine synthase inhibitors or methionine synthesis inhibitors are tested for their ability to reduce homocysteine levels in animal models, including humans.

For the treatment of infectious diseases such as *Pneumocystis carnii*, methods such as those described by WO 2005/000239 are used. Methods for modulating virulence have also been described (WO 2000/074686). Other infectious disease treatments use methods known to those skilled in the art. Imaging studies follow the methods described by Deng et al., 2011 S-11C-methyl-L-cysteine: a new amino acid PET tracer for cancer imaging. J Nucl Med. 2011 February; 52(2):287-93. Epub 2011 Jan. 13.

7. EXAMPLES

In order to more fully illustrate the invention, the following examples are provided.

7.1. Example

Identification of Active Microcin Methionine Analogue or Methionine Synthesis Inhibitors In order to further assess new microcin producing strains or those strains identified above, methods known to those skilled in the arts are employed. Briefly, the culture supernatant is separated from the bacteria by centrifugation, followed by filtration through a sterile 0.22 micrometer filter.

The effect of the microcins, methionine analogues or methionine synthesis inhibitors on in vitro cytotoxicity toward cancer cells is determined using standard cell culture techniques and cytotoxicity assays such as MTT (3-(4,5-Dimethylthiazol-2-yl)-2,5-diphenyltetrazolium bromide, a tetrazol; Mosmann 1983; J. Immunol Methods 65:55-63). The contribution of the microcins, methionine analogues or methionine synthesis inhibitors and cytotoxic agents or methioninase are determined individually and in combination. Combination effects, including antagonism, additivity or synergy may determined using the median effect analysis (Chou and Talaly 1981 Eur. J. Biochem. 115: 207-216) or other standard methods (White et al., 1996, Antimicrobial Agents and Chemotherapy 40: 1914-1918; Brenner, 2002, Annals of Oncology 13: 1697-1698; Berenbaum M C. 1989. What is synergy? Pharmacol Rev. 41(2): 93-141; Greco W R, Bravo G, Parsons J C. 1995. The search for synergy: a critical review from a response surface perspective. Pharmacol Rev. 47(2): 331-85); Zhao et al., 2004, Evaluation of Combination Chemotherpy, Clin Cancer Res 10: 7994-8004; Loewe and Muischnek, 1926. Effect of combinations: mathematical basis of the problem, Arch. Exp. Pathol. Pharmakol. 114: 313-326). The assay may also be used to determine synergy, additivity or antagonism of two or more bacterial methionine analogue microcins, or in combination with methioninase. The assay may also be used to determine synergy, additivity or antagonism a bacterial methionine analogue microcins together with microtubule depolymerizing agents (vincristine, vinorelbine, vinblatine and mebendazole) conventional small molecule cytotoxin (e.g., cisplatin, doxorubicin, irinotecan, paclitaxel; Chu and DeVita, 2010, Physicians' Cancer Chemotherapy Handbook, Jones and Bartlett), targeted therapeutic (e.g., imatinib, irissa, cetuximab), proteosome inhibitors (e.g., bortezomib), mTOR inhibitors or PARP inhibitors.

7.2. Example

Purification of Microcin Methionine Analogue or Methionine Synthesis Inhibitors Active microcin methionine analogue or methionine synthesis inhibitors can be further purified as described by Morin et al., 2011 (Antimicrobial Agents and Chemotherapy, 55: 997-1007), wherein purified microcin is obtained by solid-phase extraction on Sep-Pak plus environmental C18 cartridges, followed by concentration under vacuum and then by subjecting it to a separation by C8 Reverse Phase-HPLC. A final C8 reverse phase column is used and eluted with 50% (vol/vol) acetonitrile-0.1% (vol/vol) trifluoroacetate. After the separation anti-microbial activity is determined. The material may be dried under vacuumed and redissolved in a pharmaceutically acceptable carrier for additional assays inclining dose-ranging tolerability studies and antitumor efficacy.

7.3. Example

Dose-Ranging Tolerability Study

In order to assess the potency of a substantially purified methionine analogue microcin, a standard dose-ranging study is performed. Dose escalation begins at 1 mg/kg Q2Dx3 X2, given IV and followed for 2 weeks post administration. The general appearance and body weight are used as in-life indicators of general health, and organ weights used at the end of the study period. Deviations of less than 15% of normal are deemed sufficiently safe to proceed to higher doses. If, at 1 mg/kg Q2Dx3 X2 is shown to be toxic, the dose will be lowered by 50% until a safe dose is determined. If, at 1 mg/kg Q2Dx3 X2 is shown to be non-toxic, the dose will be increased by 50% until a safe, maximally tolerated dose is determined.

7.4. Example

Anti-Tumor Effect(s) of Microcin Methionine Analogues

A tumor type known to be sensitive to methionine may be selected, such as the human lung cancer cell line H460 (Miki et al., 2000, Cancer Gene Therapy 7: 332-338). Tumor cells are implanted into nude mice and allowed to progress until palpable. Following palpation, all tumors are measured by calipers 3x/week. Animals, 6 per group, are placed into 3 groups:
1) control, saline treatment,
2) 50% MTD dose of methionine analogue microcin, and
3) MTD dose of methionine analogue microcin.

Tumor volume is evaluated over time. A significant retardation in tumor growth such that the treatment group is <50% of the untreated control group, or reduction in tumor volume considered the equivalent of one log cell kill.

In vivo studies (G. K. Schwartz (ed) 2005, Combination cancer therapy: Modulators and potentiators, Human Press, Totowa, N.J., 284 pp.; B. A. Teicher and P. A. Andrews (eds.) 2004, Anticancer drug development guide, Preclinical screening, clinical trials and approval, Second Edition, Humana Press, Totowa, N.J., 450 p.; Teicher (ed.) 2002, Tumor models in cancer research, Human Press, Totowa, N.J., 690 p) may also be performed with antiangiogenic inhibitors such as Avastin, combrettastatin, thalidomide.

In this description, several preferred embodiments were discussed. Persons skilled in the art will, undoubtedly, have other ideas as to how the compositions and methods described herein may be used. It is understood that this broad invention is not limited to the embodiments discussed herein. All references cited above are expressly incorporated herein by reference in their entirety.

What is claimed is:

1. A method of treating an animal, comprising administering an effective dose of at least one substantially purified, pharmaceutically acceptable microcin methionine analogue or microcin methionine synthesis inhibitor except microcin 15m or microcin M15 or a microcin from E. coli LP15, to an animal having at least one of a tumor, hyperhomocysteinemia, and an infectious disease, in an effective amount to thereby respectively inhibit tumor growth, treat hyperhomocysteinemia, or treat the infectious disease.

2. The method according to claim 1, further comprising administering the pharmaceutically acceptable microcin methionine analogue or microcin methionine synthesis inhibitor with tumor growth inhibitory ability in combination with a microtubule depolymerizing agent.

3. The method according to claim 1, further comprising administering the at least one pharmaceutically acceptable microcin methionine analogue, or microcin methionine synthesis inhibitor in combination with methioninase.

4. The method according to claim 1, wherein the animal has an infectious disease caused by a fungus.

5. The method according to claim 4, wherein the fungus comprises at least one of *Pneumocystis carnii* and *Candida albicans*.

6. The method according to claim 1, wherein the animal has a tumor comprising a neoplasia originating in a tissue selected from the group consisting of stomach, colon, rectum, liver, pancreas, lung, breast, cervix uteri, corpus uteri, ovary, prostate, testis, bladder, kidney, brain, central nervous system, head, neck, throat, or selected from the group consisting of Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, esophagus, larynx, kidney and lymphoma cancer.

7. The method according to claim 1, wherein the pharmaceutically acceptable microcin methionine analogue or microcin methionine synthesis inhibitor comprises a microcin which is at least one of (a) derived from *E. coli* LP 136, D93, V517; and (b) encoded by at least one plasmid selected from the group consisting of plasmid pCP101, pCP102, pCP103, pCP104, pCP105, pCP106, and pVA517C.

8. A method of treating an animal, comprising:
determining a presence of a disease selected from the group consisting of a neoplasia, hyperhomocysteinemia, and an infectious disease;
administering a regimen of effective doses of a pharmaceutically acceptable composition comprising at least one of isolated microcin methionine analogues, and or microcin methionine synthesis inhibitors except microcin 15m or microcin M15 or a microcin from *E. coli* Lp15, to an animal having the disease, over a sufficient time to achieve an effective treatment of the disease; and
monitoring the treatment by performing at least one laboratory test to determine at least one of a neoplasm size, a homocystiene level, and a presence of an infectious organism.

9. The method according to claim 8, wherein the effective doses are provided in unit dosage form.

10. A pharmaceutical composition for administration to a human having a neoplasm, comprising at least one pharmaceutically acceptable agent selected from the group consisting of microcin methionine analogues and microcin methionine synthesis inhibitors except microcin 15m or microcin M15 or a microcin from *E. coli* LP15, which has been substantially purified, in a sterile unit dose form selected from the group consisting of an intravenous dosage vial, an oral unit dosage form, and a parenteral dosage form, in an amount sufficient to achieve significant retardation in tumor growth and within a maximum tolerated dose, which is diluted with or compounded with at least one other active or inactive ingredient.

11. The pharmaceutical composition according to claim 10, further comprising a pharmaceutically acceptable excipient, additive or carrier.

12. The pharmaceutical composition according to claim 10, wherein the unit dose form comprises an intravenous dosage vial.

13. The pharmaceutical composition according to claim 10, wherein the unit dosage form comprises an oral unit dosage form.

14. The pharmaceutical composition according to claim 10, wherein the unit dosage form comprises a parenteral dosage form.

15. The pharmaceutical composition according to claim 10, where the pharmaceutically acceptable agent comprises at least one of (a) derived from *E. coli* LP 136, D93, V517; and (b) encoded by at least one plasmid selected from the group consisting of pCP101, pCP102, pCP103, pCP104, pCP105, pCP106, and pVA517C.

16. The pharmaceutical composition according to claim 10, further comprising a microtubule depolymerizing agent.

17. The pharmaceutical composition according to claim 16, wherein the microtubule depolymerizing agent comprises at least one of vincristine, vinorelbine, vinblatine and mebendazole.

18. The pharmaceutical composition according to claim 10, further comprising methioninase.

19. The pharmaceutical composition according to claim 10, wherein the at least one pharmaceutically acceptable agent comprises a purified microcin methionine analog.

20. The pharmaceutical composition according to claim 10, wherein the pharmaceutically acceptable agent comprises a purified microcin methionine synthesis inhibitor.

* * * * *